United States Patent [19] [11] 4,171,967
Parham et al. [45] Oct. 23, 1979

[54] ARBORICIDE

[75] Inventors: Martin R. Parham, Reading; Brian G. White, Crowthorne, both of England

[73] Assignee: Imperial Chemical Industries Limited, London, England

[21] Appl. No.: 849,656

[22] Filed: Nov. 8, 1977

[30] Foreign Application Priority Data

Nov. 16, 1976 [GB] United Kingdom ............. 47665/76

[51] Int. Cl.² .......................... A01N 5/00; A01N 9/22
[52] U.S. Cl. ............................................ 71/74; 71/94
[58] Field of Search ................................... 71/94, 74

[56] References Cited
U.S. PATENT DOCUMENTS 2,972,528  2/1961  Brian et al. ...................... 71/94
3,150,954  9/1964  Wheeler ........................... 71/94
3,332,959  7/1967  Braunholtz ..................... 71/74 X Primary Examiner—Catherine L. Mills
Attorney, Agent, or Firm—Cushman, Darby & Cushman

[57] ABSTRACT

A process of killing or defoliating trees, which comprises applying to the tree a bipyridylium zwitterion of the formula:

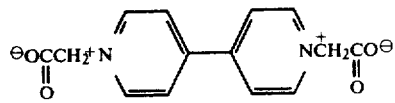

or an acid addition salt thereof.

6 Claims, No Drawings

ARBORICIDE

This invention relates to a method for killing or defoliating trees using a zwitterionic bipyridylium derivative, and to arboricidal or tree defoliant compositions containing the zwitterionic derivative.

There are occasions in forestry and other agricultural practices where it is desired to kill or defoliate a tree. The term "tree" as used herein refers to perennial plants with a woody self-supporting stem.

A number of compounds have been used in the past to kill trees. Some of these are arsenical compounds such as cacodylic acid. By reason of their mammalian toxicity, arsenical compounds are now considered undesirable for such use. An alternative is picloram (4-amino-3,5,6-trichloropicolinic acid) but this compound is highly mobile and persistent in the soil; consequently since it is a strong inhibitor of photosynthesis, it could damage non-target organisms. 2,4,5-T (2,4,5-trichlorophenoxyactic acid) has also been used, but its preparation can result in the formation of a highly toxic dioxin and so commercial manufacture of 2,4,5-T may soon be discouraged. The usual methods of applying these arboricides are by injection into the trunk of the tree or by foliar application.

We have discovered a bipyridylium zwitterion which has tree defoliant and arboricidal activity. This bipyridylium zwitterion can be applied to the exposed sapwood of the tree (e.g. a bore hole, frill or axe cut or other incision) or to the unprepared bark; alternatively it can be applied by spraying on to the foliage from, for example, an aeroplane.

The invention therefore provides a method of killing or defoliating trees, which comprises applying to the tree a bipyridylium zwitterion of the formula:

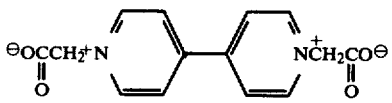

or an acid addition salt thereof.

The above formula is considered to represent the structure of the bipyridylium zwitterion in solutions which are not strongly acid. However, in strongly acid solution the carboxylate groups will be protonated and the compound will exist as its acid addition salt. For example, in concentrated hydrochloric acid, the bipyridylium zwitterion will be converted to the dihydrochloride addition salt, having the following formula:

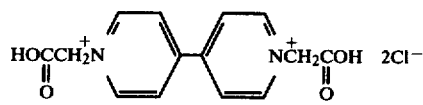

When isolated in the solid state, the bipyridylium zwitterion will also normally be obtained in the form of its acid addition salts, for example the dihydrochloride, the dihydrobromide, and the dihydroiodide.

The use of the bypyridylium zwitterion is advantageous over prior art arboricides like picloram because the bipyridylium zwitterion is deactivated in the soil and so presents no residue problems. Chemical agents for killing or defoliating trees may be useful in a variety of forestry operations.

Thus, if a tree intended for pulp manufacture is killed and then left standing to season, the handling of the dead tree is easier, since the bark can be readily stripped from the dead tree (unlike that of a recently felled tree) and since the dead tree loses water and so becomes lighter in weight; the transport and other handling costs are thus less.

In the cultivation of conifers and other trees, it is usually necessary to thin the forests. This can be done either by selecting the weaker trees for felling or by removing completely one in say four rows. This operation has hitherto been done by applying one of the above known arboricides but these arboricides have the previously mentioned disadvantages. The present invention, when applied by injection or by the bark penetration technique, is suitable for this thinning operation. This "chemical thinning" of forests has the advantage over selective thinning by mechanical removal of the weaker trees that the labour requirement of chemical thinning is much less.

The present invention can also be used to clear scrubland from, for example, blackberry, gorse and rhododendron, and to thin pines along power-lines and rights of way.

The bipyridylium zwitterion when used as a defoliant finds utility in coppice forestry and the production of essential oils from tree foliage. It is particularly applicable to eucalyptus cultivation in, for example, South Africa where the eucalyptus is used for paper making and for extraction of essential oil from the foliage. The eucalpytus leaves should be removed before the tree enters the paper making process. The invention can be used to defoliate the main tree in a coppice before it is removed; the root system of that tree can then be allowed to re-sprout without incurring damage from the chemical defoliant.

In some cattle areas, for example in Australia and South America, plants such as leguminous thorny bushes and eucalyptus tend to take over land intended for cattle husbandry. The bipyridylium zwitterion can be used to kill these undesirable growths. In this case, unlike in coppice forestry, it is desired to prevent regrowth; this can be done by applying a higher dose of zwitterion, or by mixing it with another herbicide such as diquat.

Rubber trees (particularly in Malaya) are susceptible at certain times of the year to fungal attack through their leaves. In the past rubber trees have been defoliated at that time of the year, with cacodylic acid, so avoiding fungal attack. The rubber trees have then been allowed to re-foliate at the safe time of the year. The treatment with cacodylic acid is now unacceptable for toxicity reasons.

As indicated above, the zwitterion can be applied to the exposed sapwood of the tree or to the untreated bark, or it can be applied by foliar spraying.

The exposed sapwood may comprise an area in which the bark has been removed, or it may be a frill or axe cut or a downwardly sloping bore hole. In the former three cases, a solution of the zwitterion can be sprayed, poured or brushed on the sapwood while in the latter case the zwitterion may be poured into the borehole in the form of an aqueous solution. Automatic injection axes can be used to apply a solution of the zwitterion.

The rate at which the zwitterion is applied to the tree depends upon the species of tree to be treated, the size of the tree and the speed with which it is desired the tree should die or defoliate. The amount of zwitterion to be applied will lie within the range from 2 to 4500 milligrams per tree for many tree species. Conifers are particularly vulnerable to the zwitterion; 4 mg can kill a pine tree 10 meters in height in two weeks. Birch trees require more zwitterion than this; 50 mg will usually be required to kill a birch tree of height 6 meters in about the same time. Eucalyptus trees need even more, often requiring 1500 mg or more to achieve defoliation.

In trees of less than 5 meters in height, the grain spirality may not be adequate to ensure diffusion of the zwitterion throughout the crown of the tree. In such cases, it is preferable to introduce the zwitterion into the tree at more than one point. Thus, each of two trees of species *Picea abies* less than 5 meters in height were treated with 10 milligrams of zwitterion injected into a single point at chest height. Branches which were anatomically above the injection point were killed, whereas other branches on the same tree remained alive. However, to similar trees injected with 5 milligrams of zwitterion into each of two points on opposite sides of the trees (giving a total of 10 milligrams per tree) were completely killed.

The zwitterion can be in the form of an aqueous solution particularly when intended for application to the exposed sapwood of the tree. For foliar spray application, compositions containing conventional additives can be used. Such additives usually comprise surface active agents. Examples of suitable surface active agents are discussed in British Patent specification No. 1,395,502, the disclosure of which Specification is incorporated herein by reference.

Compositions suitable for use by the bark penetrant technique can contain surface-active agents and organic liquids in order to assist the application of the zwitterion to the bark and its penetration through the bark and into and through the sapwood (i.e., xylem) of the tree.

Thus, the penetration of aqueous solutions may be assisted by including one or more surface-active agents in the solution. These can be non-ionic, anionic or cationic surface-active agents. The choice of surface-active agent is of course within the knowledge of those skilled in the art. The non-ionic surface-active agent can be the condensation products of ethylene oxide with fatty alcohols such as oleyl alcohol and cetyl alcohol, or with alkyl phenols such as octyl- or nonyl-phenol and octyl-cresol. Other non-ionic agents are the partial esters derived from long chain fatty acids and hexitol anhydrides, for example sorbitan monolaurate; the condensate products of the said partial esters with ethylene oxide, and the lecithins. Examples of cationic surface-active agents include quaternary salts (for example cetyltrimethylammonium bromide or chloride) and condensates of ethylene oxide with amines, for example the substances sold under the trade names Ethomeen, Ethoduomeen, Ethoquad, Duoquad and Arquad. The amount of surface-active agent used in the aqueous solution may be varied between wide limits but conveniently is often from 10 to 100 grams per liter of solution.

Particular examples of aqueous solutions containing surface-active agents to assist the zwitterions to penetrate the bark include the compositions disclosed in British Patent specification No. 998,264, the disclosure of which Specification is incorporated hereby by reference.

Examples of organic liquids for mixing with an aqueous solution of the bipyridylium zwitterion to assist its penetration through bark include dimethylsulphoxide, diesel oil, ground nut oil, tetrahydrofurfuryl alcohol, polyethylene glycol and an alkyl ester of a phthalic acid (the alkyl moiety thereof having at least four carbon atoms), e.g. dibutyl phthalate. The mixtures preferably also contain an emulsifier to assist in dispersing the organic liquid in the solution of the zwitterion.

In order to assist in localising the compositions (for example those comprising dibutyl phthalate) on the tree bark, so as to maintain a high concentration of zwitterion in a small area, thickening agents may be added to convert the composition into a paste or a gel. These pastes have the advantage over simple aqueous compositions that they are not highly fluid and will not run off down the bark of the tree when applied thereto.

Thickened formulations may also be prepared from aqueous solutions of the zwitterion, optionally containing surface-active agents, by adding conventional thickening agents.

Aqueous solutions of the zwitterion can also be dispersed in an oil in the form of an invert emulsion.

The zwitterion can be dispersed in an emulsion paint. Such compositions may be prepared by simply mixing an aqueous solution of the zwitterion and the emulsion paint. The use of such compositions provides a lasting indication that a tree has been treated, and thus enables the forester to avoid treating a tree twice.

The zwitterion can therefore be used in the form of an arboricidal or tree defoliant composition comprising the zwitterion and a carrier or diluent. The amount of zwitterion in the composition is not critical but may be for example from 5 to 200 grams per liter of the composition.

The bipyridylium zwitterion used in the process of the invention is conveniently prepared by acid hydrolysis of a compound of the following formula:

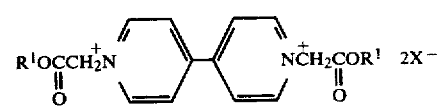

wherein $R^1$ is an alkyl radical, preferably of 1 to 4, carbon atoms, for example a methyl or ethyl radical, and X is a halide. Direct reaction of chloroacetic acid with 4,4'-bipyridyl is unsatisfactory, since a proportion of the product obtained by this method consists of the 1,1'-dimethyl-4,4'-bipyridylium quaternary salt, arising from decarboxylation during the quaternisation reaction.

A description of a process for preparing the hydrochloride salt of the bipyridylium zwitterion is given below.

4,4'-Bipyridyl (156 g) was heated with ethyl chloroacetate (245 g) in dry dimethylformamide (400 ml) to 90°-100° C. After 2 hours a further quantity of ethyl chloroacetate (123 g) was added and the mixture heated a further 2.5 hours at 120° C. The solution was cooled, diluted with chloroform (400 ml), stirred a short time at 0° C., and the solid collected, washed with chloroform and dried. The 1,1'-di-ethoxycarbonylmethyl-4,4'-bipyridylium dichloride so obtained (340 g) was dissolved in concentrated hydrochloric acid and heated under reflux for 3 hours. The mixture was cooled to 0° C., acetone (200 ml) slowly added, and the grey solid collected, washed with acetone, and dried, giving 1,1'-dicarboxymethyl-4,4'-bipyridylium dichloride.

The invention is illustrated by the following Examples.

EXAMPLE 1

This Example illustrates the relatively much greater toxicity of the bipyridylium zwitterion towards trees as compared with the closely related bipyridylium quaternary salt paraquat.

Pine trees (*Pinus sylvestris*) of height about 10 meters were injected at two sites with various amounts of paraquat. Similar trees were injected in the same way with various amounts of the bipyridylium zwitterion. It was found that 2×2 mg of the zwitterion was sufficient to cause death of the trees in 2 to 3 weeks, while 2×500 mq of paraquat caused no deaths.

EXAMPLE 2

Compound 1 was applied to various tree species. The results are shown in the Table.

EXAMPLE 4

This Example illustrates the defoliation of eucalyptus trees (*Eucalyptus camaldulensis*) by application of the bipyridylium zwitterion. The trees were three to four years old, 10 to 15 centimeters in diameter, and 4.5 to 7.5 meters high. Cuts were made around the base of the tree, 3.5 cm long and 1 cm deep, spaced 1 cm apart around the circumference 20 cm above ground level and angled at about 45°. The bipyridylium zwitterion was applied as an aqueous solution to the cuts. The bipyridylium zwitterion was applied at rates of 1.5 grams and 4.5 grams per tree. The higher rate gave 80 to 90% leaf desiccation within 4 weeks. Complete leaf desiccation was observed after 71 days with the trees treated at the 1.5 gram application rate. The trees were observed for 545 days, at the end of which time the foliage was re-growing.

In a similar experiment, a mixture of the bipyridylium

TABLE

| TEST SPECIES | HEIGHT (METERS) | APPLICATION METHOD | DOSE/TREE+ | TIME OF APPLICATION | EFFECT OBSERVED* |
| --- | --- | --- | --- | --- | --- |
| Pine (*Pinus slyvestris*) | 10 | 2 bore-holes | 2 mg each | Spring of two successive years | Death plus defoliation within two weeks |
| Eucalyptus | — | frill-cut | 400 mg | Spring or Autumm | Rapid defoliation in 2-3 weeks. Regrowth below frill after ca. 6 months |
| Poplar | 5 | 1 bore-hole | 2 mg | Spring | Severe foliar phytotoxicity one side only. Growth reduced. Some leaf drop |
| Blackcurrant | 0.7 | One side shoot torn off. Aqueous solution seeped into single stem. | 0.5 mg | Spring | Growth retarded by 50% over 3 months Some leaf drop local to site of application |
| Blackcurrant | 1 | As for blackcurrant | up to 9 mg | Summer | Severe local foliar scorch |
| Apple | * | cut in bark | 50 and 100 mg | Summer | Slight to moderate phytotoxicity above treatment zone. Sucker growth at base not inhibited |
| Holm Oak | | Series of chisel incisions, | total 1 g | Summer | Death of tree |

*These trees were about 4 years old
+ Optimum doses may be lower than the figures given
*In some cases, additional effects are noticed later on.

EXAMPLE 3

Experiments were carried out in which an aqueous solution of the bipyridylium zwitterion was injected into the trunks of mature trees (25 to 40 years old and 20 to 30 meters in height). The table below gives the lethal dose which was determined for various tree species in this way.

| Tree Species | Lethal dose of bipyridylium zwitterion (milligrams per tree) |
| --- | --- |
| Pinus spp. | 50 |
| Picea abies | 100 |
| Picea amorica | 100 |
| Larix decidua | 100 |
| Tsuga heterophylla | 100 |
| Chamaecyparis lawsonii | 200 |
| Abies nobilis | 200 |
| Cupressus lawsonii | 200 |
| Sequoia gigantea | 300 | zwitterion (1.5 grams) and diquat (1.5 grams) was applied in aqueous solution. Complete leaf desiccation was observed within 28 days. The trees were observed for 497 days, at the end of which time no regrowth was observed.

EXAMPLE 5

This Example illustrates compositions for use in the invention containing thickening agents.

Composition 1

| | |
| --- | --- |
| Bipyridylium zwitterion (as dihydrochloride) | 200 g |
| Superfloc N100 | 25 g |
| Aluminum chloride | 1 g |
| Water | to 1 liter |

Superfloc is a polyacrylamide of molecular weight 5 to 6 million.

Composition 2

| | |
|---|---|
| Bipyridylium zwitterion (as dihydrochloride) | 200 g |
| HLB 18 | 50 g |
| Dibutyl phthalate | 400 g |
| Attagel 50 | 200 g |
| Water | to 1 liter |

Attagel 50 is a grade of colloidal attapulgite clay. HLB 18 is a mixture of emulsifiers comprising 60% of Tween 20 and 40% of Tween 80.

A similar composition may be prepared using Hydral 710 (200 grams) in place of the Attagel 50. Hydral 710 is a grade of finely divided alumina.

We claim:

1. A process of killing or defoliating trees, which comprises applying to the tree an effective amount of a bipyridylium zwitterion of the formula:

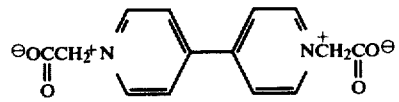

or an acid addition salt thereof.

2. A process as claimed in claim 1 wherein the bipyridylium zwitterion is applied to a site on the tree at which the sapwood has been exposed by removing the bark therefrom.

3. A process as claimed in claim 1 wherein the rate of application of the bipyridylium zwitterion is from 2 milligrams to 4500 milligrams per tree.

4. A process as claimed in claim 1 wherein the bipyridylium zwitterion is applied in the form of an aqueous solution.

5. A process as claimed in claim 4 wherein the aqueous solution contains a surface-active agent.

6. A process as claimed in claim 4 wherein the aqueous solution comprises a thickening agent.